(12) United States Patent
DeVega

(10) Patent No.: US 8,936,571 B2
(45) Date of Patent: Jan. 20, 2015

(54) ILLUMINATED SYRINGE

(76) Inventor: Laura DeVega, Dallas, TX (US)

(*) Notice: Subject to any disclaimer, the term of this patent is extended or adjusted under 35 U.S.C. 154(b) by 457 days.

(21) Appl. No.: 12/932,602

(22) Filed: Feb. 28, 2011

(65) Prior Publication Data
US 2011/0196312 A1   Aug. 11, 2011

Related U.S. Application Data

(63) Continuation-in-part of application No. 12/079,958, filed on Mar. 31, 2008, now Pat. No. 7,896,838.

(51) Int. Cl.
*A61M 5/00* (2006.01)
*A61M 5/42* (2006.01)
*A61M 5/31* (2006.01)

(52) U.S. Cl.
CPC ............. *A61M 5/427* (2013.01); *A61M 5/3134* (2013.01); *A61M 5/3135* (2013.01); *A61M 2205/587* (2013.01)
USPC .................................................. 604/116

(58) Field of Classification Search
USPC ....................... 604/20, 21, 187, 116
See application file for complete search history.

(56) References Cited

U.S. PATENT DOCUMENTS

| | | | | |
|---|---|---|---|---|
| 5,586,976 A | * | 12/1996 | Coutoumanos | 604/192 |
| 5,599,302 A | * | 2/1997 | Lilley et al. | 604/68 |
| 5,899,889 A | * | 5/1999 | Futagawa et al. | 604/232 |
| 2005/0080384 A1 | * | 4/2005 | Green | 604/218 |

* cited by examiner

*Primary Examiner* — Bhisma Mehta
*Assistant Examiner* — Bradley Osinski
(74) *Attorney, Agent, or Firm* — Thrasher Associates

(57) ABSTRACT

The invention is an apparatus comprising of a syringe, a plunger and a circuit for the purpose of activating a light source to illuminate a target area for application of the contents of the syringe in low-light or no-light situations.

5 Claims, 5 Drawing Sheets

ILLUMINATED SYRINGE

CROSS-REFERENCE TO RELATED APPLICATIONS

This application is a continuation in part of, and claims priority to, U.S. patent application Ser. No. 12/079,958, now U.S. Pat. No. 7,896,838, to DeVega filed Mar. 31, 2008.

TECHNICAL FIELD

The present invention relates to syringe devices.

Problem Statement

Interpretation Considerations

This section describes the technical field in more detail, and discusses problems encountered in the technical field. This section does not describe prior art as defined for purposes of anticipation or obviousness under 35 U.S.C. section 102 or 35 U.S.C. section 103. Thus, nothing stated in the Problem Statement is to be construed as prior art.

Discussion

Parents needing to dispense medications orally to infants and children are often faced with the problem of dispensing the liquid in low-light conditions. This is typically due to a child or incapacitated adult requiring medication during the night. Of course, turning on the light at night can disturb a resting person, thus hampering recovery and perhaps disturbing an entire family. Conversely, without sufficient light, medication may be administered clumsily. Indeed, the dispersing person may not be able to tell if the patient/child/animal actually received the liquid. Similar problems occur when dispensing liquid medication to animals in a dark area. The present invention solves these and related problems.

BRIEF DESCRIPTION OF THE DRAWINGS

Various aspects of the invention, as well as at least one embodiment, are better understood by reference to the following EXEMPLARY EMBODIMENT OF A BEST MODE. To better understand the invention, the EXEMPLARY EMBODIMENT OF A BEST MODE should be read in conjunction with the drawings in which.

AN EXEMPLARY EMBODIMENT OF A BEST MODE

Figure 1A:
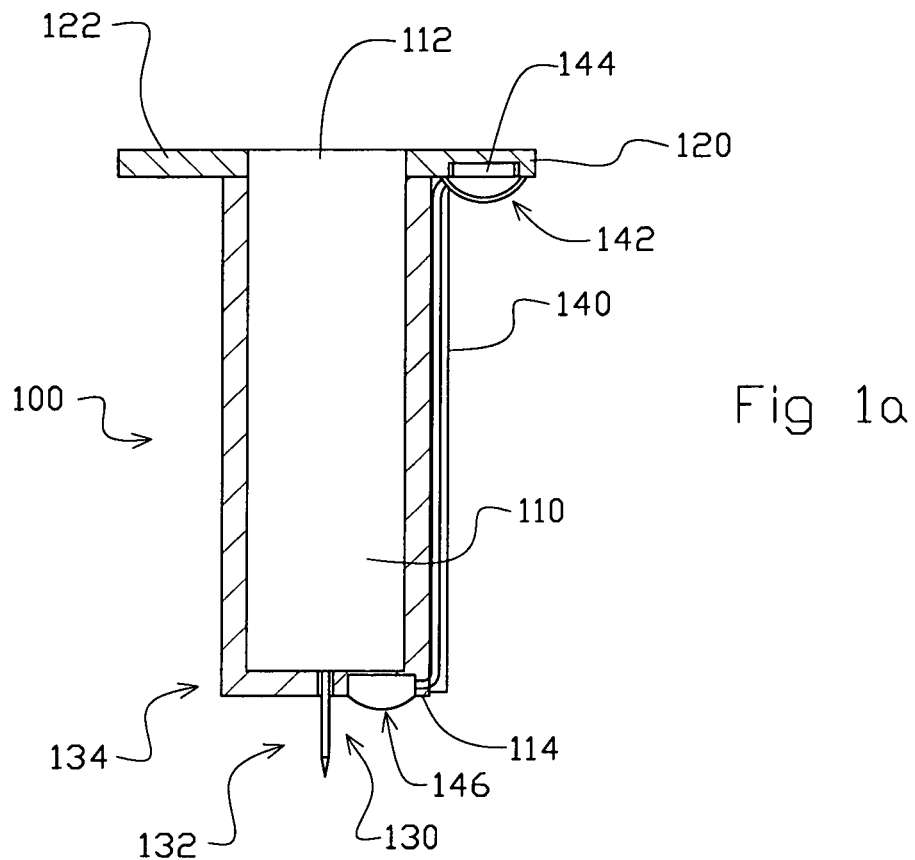
FIG. 1a shows a side-cut view of one embodiment.

When reading this section (An Exemplary Embodiment of a Best Mode, which describes an exemplary embodiment of the best mode of the invention, hereinafter "exemplary embodiment"), one should keep in mind several points. First, the following exemplary embodiment is what the inventor believes to be the best mode for practicing the invention at the time this patent was filed. Thus, since one of ordinary skill in the art may recognize from the following exemplary embodiment that substantially equivalent structures or substantially equivalent acts may be used to achieve the same results in exactly the same way, or to achieve the same results in a not dissimilar way, the following exemplary embodiment should not be interpreted as limiting the invention to one embodiment.

Likewise, individual aspects (sometimes called species) of the invention are provided as examples, and, accordingly, one of ordinary skill in the art may recognize from a following exemplary structure (or a following exemplary act) that a substantially equivalent structure or substantially equivalent act may be used to either achieve the same results in substantially the same way, or to achieve the same results in a not dissimilar way.

Accordingly, the discussion of a species (or a specific item) invokes the genus (the class of items) to which that species belongs as well as related species in that genus. Likewise, the recitation of a genus invokes the species known in the art. Furthermore, it is recognized that as technology develops, a number of additional alternatives to achieve an aspect of the invention may arise. Such advances are hereby incorporated within their respective genus, and should be recognized as being functionally equivalent or structurally equivalent to the aspect shown or described.

Second, the only essential aspects of the invention are identified by the claims. Thus, aspects of the invention, including elements, acts, functions, and relationships (shown or described) should not be interpreted as being essential unless they are explicitly described and identified as being essential. Third, a function or an act should be interpreted as incorporating all modes of doing that function or act, unless otherwise explicitly stated (for example, one recognizes that "tacking" may be done by nailing, stapling, gluing, hot gunning, riveting, etc., and so a use of the word tacking invokes stapling, gluing, etc., and all other modes of that word and similar words, such as "attaching"). Fourth, unless explicitly stated otherwise, conjunctive words (such as "or", "and", "including", or "comprising" for example) should be interpreted in the inclusive, not the exclusive, sense. Fifth, the words "means" and "step" are provided to facilitate the reader's understanding of the invention and do not mean "means" or "step" as defined in .sctn.112, paragraph 6 of 35 U.S.C., unless used as "means for-functioning-" or "step for-functioning-" in the Claims section.

Of course, the foregoing discussions and definitions are provided for clarification purposes and are not limiting. Words and phrases are to be given their ordinary plain meaning unless indicated otherwise.

Discussion of the Figures

Figure 1B:
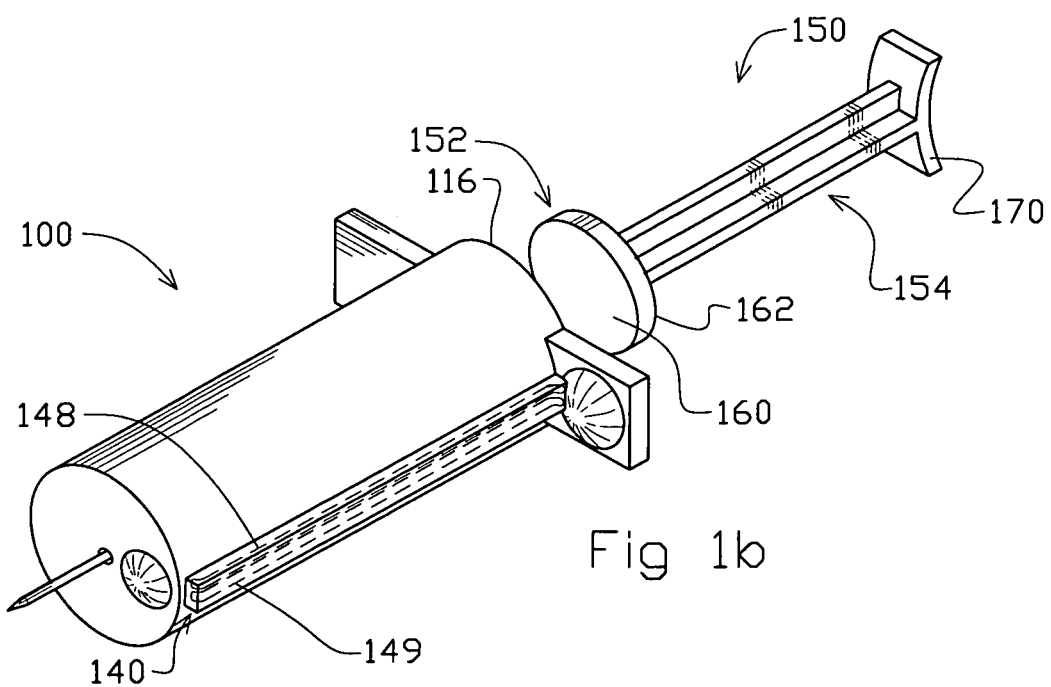
FIG. 1b shows an isometric view of the embodiment, including a syringe plunger.

The invention is better appreciated by examining the simultaneous figures of FIGS. 1a and 1b. A syringe 100 is generally cylindrical in shape and has an interior cylinder 110, open at a first end 112 that defines an opening, and narrowed to an aperture 130 at a second end, which may be adapted to provide for the attachment of a hypodermic needle 132.

A fluid in the interior chamber of the cylinder 110 is forcibly passable through the aperture 130 at the second end via a plunger 150 which is comprised of a shaft 154, a piston 160 at a first end 152 and a thumb accommodating terminus 170. The outer circumference 162 of the piston 150 is flush with the circumference of the syringe cylinder 110 to effect an air-tight seal of the fluid in the chamber 110. As is appreciated in the art, by applying pressure to the thumb-accommodating terminus 170, fluid may be forced through the aperture 130 of the second end of the syringe 100.

As pressure is applied to the thumb-accommodating terminus 170 the syringe 100 is typically supported by two human fingers, one on each flange 120, 122 at the first end of the syringe 112. This pressure detents the flange 120 and completes a circuit, engaging an electrical source 144 secured in a flange chamber 142. The electrical current travels via a first wire 148 contained in a sleeve 140 that transverses the syringe and couples to a LED 146 in an LED mount 114 of the second end 134. The current then travels through a second wire 149 contained in sleeve 140 that is coupled to the LED 146 and the electrical source 144 in the flange chamber 142.

Figure 2:
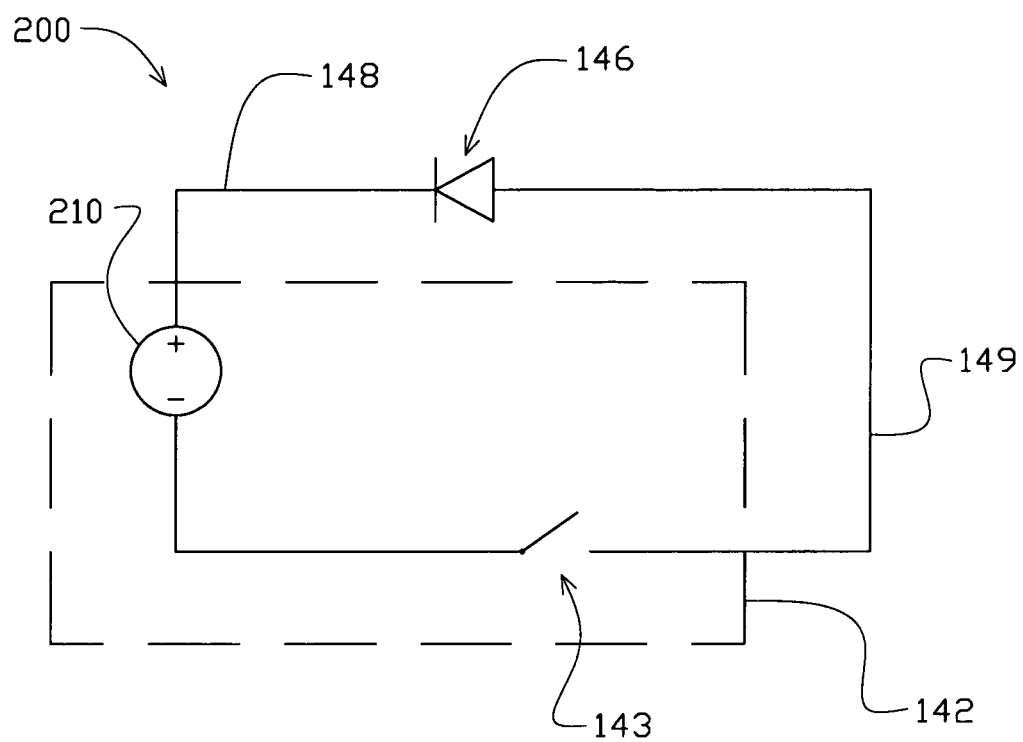
FIG. 2 is a schematic diagram of the invention.

FIG. 2 is a schematic circuit 200 of an embodiment of the invention. The circuit 200 includes a power source 210, which could be a battery or a capacitor, for example, and the power source 210 is preferably secured in the detentable portion/switch 143 of the chamber 142. Accordingly, the detentable portion 143 is illustrated as and effectively performs the function of a switch, such as a push-button switch. In the embodiment illustrated in FIG. 1, the first wire 148 and the second wire 149 are shown as components of the circuit 200 that complete the circuit to the light source 146 illustrated as a diode. The function and alternative structures of the invention are readily apparent to those of skill in the art upon reading the present disclosure.

Figure 3A:
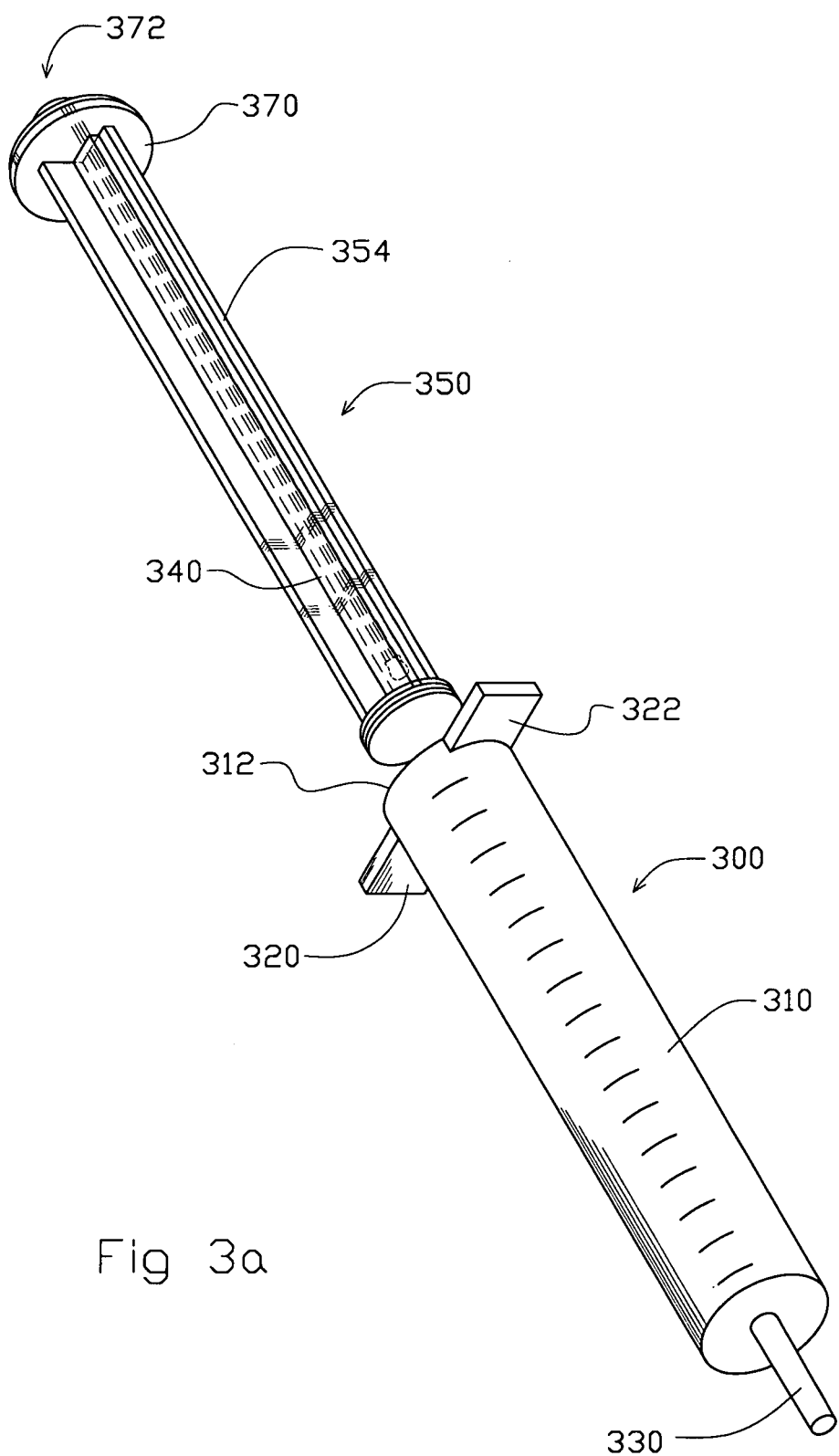
FIG. 3a illustrates an alternative embodiment of the invention that places the circuit inside a syringe piston.
Figure 3B:
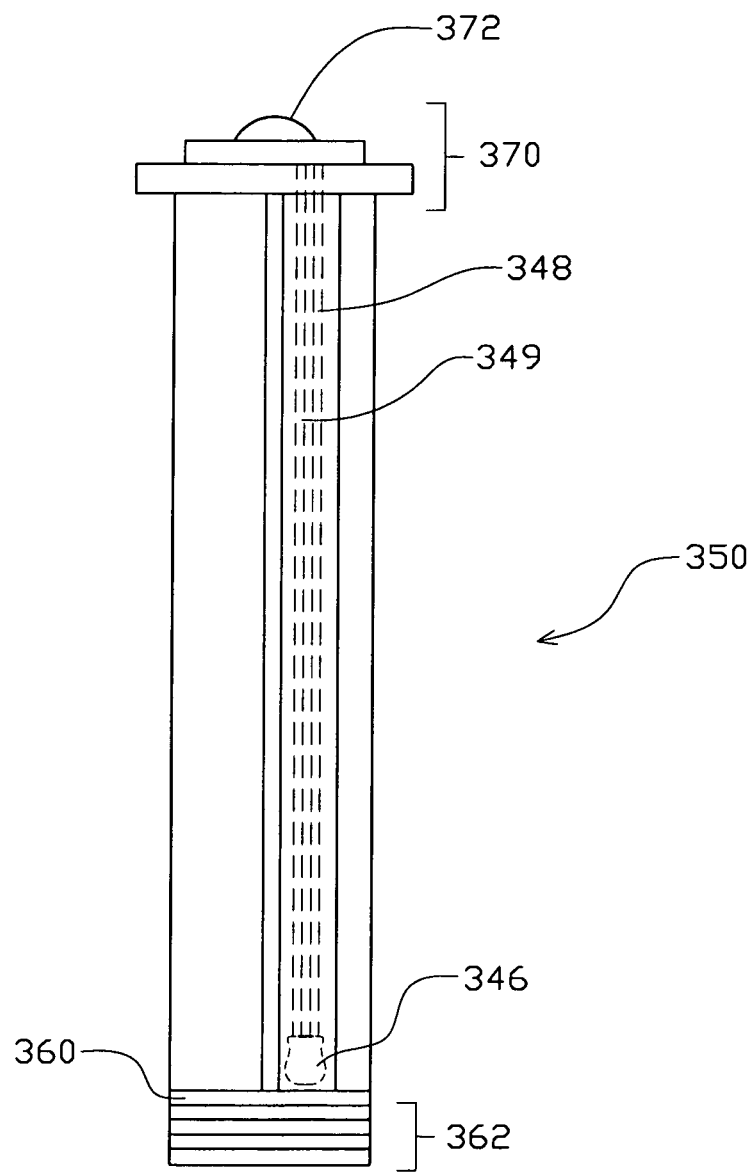
FIG. 3b illustrates the detail of the syringe piston of FIG. 3a from a side-on point of view.

An alternative embodiment of the invention is better appreciated by examining simultaneously FIGS. 3*a* and 3*b*. A syringe 300 is generally cylindrical in shape and has an interior cylinder, open at a first end 312 that defines an opening, and narrowed to an aperture/neck 330 at a second end.

A fluid in the interior chamber of the cylinder 310 is forcibly passable through the aperture 330 at the second end via a plunger 350 which is comprised of a shaft 354, a piston 360 and soft tip 362 combination at a first end and a terminus 370 at a second end. Both the piston and the tip may be substantially translucent and/or clear. As discussed in the prior embodiment and as known in the art, the outer circumference of the piston 350 is flush with the circumference of the syringe cylinder 310 to effect a fluid-tight seal of the fluid in an interior chamber. As is appreciated in the art, by applying pressure to the terminus 370, fluid may be forced through the aperture 330.

As pressure is applied to terminus 370 the syringe 300 is typically supported by two human fingers, one on each flange 320, 322. Sufficient pressure on the detentable member/switch 372 of the terminus 370 detents the detentable member/switch 372 and completes a circuit, engaging an electrical source 210 secured in the terminus 370. The electrical current travels via a first wire 348 contained in a hollow portion/sleeve 340 of plunger 350 that substantially transverses the length of the plunger 350 and couples to a light source 146, such as an LED, including LEDs of different light colors, changing light colors and/or intensities, and/or programmable LEDs. Current then travels through a second wire 349 contained in the sleeve 340 that is also coupled to the light source 346 and the electrical source 210 in the terminus 370. In an alternative embodiment, the sleeve 340 traverses the center of the plunger 350, and may incorporate more than one sleeve, more than one power source (which may be replaceable) and more than one light source.

Figure 4:
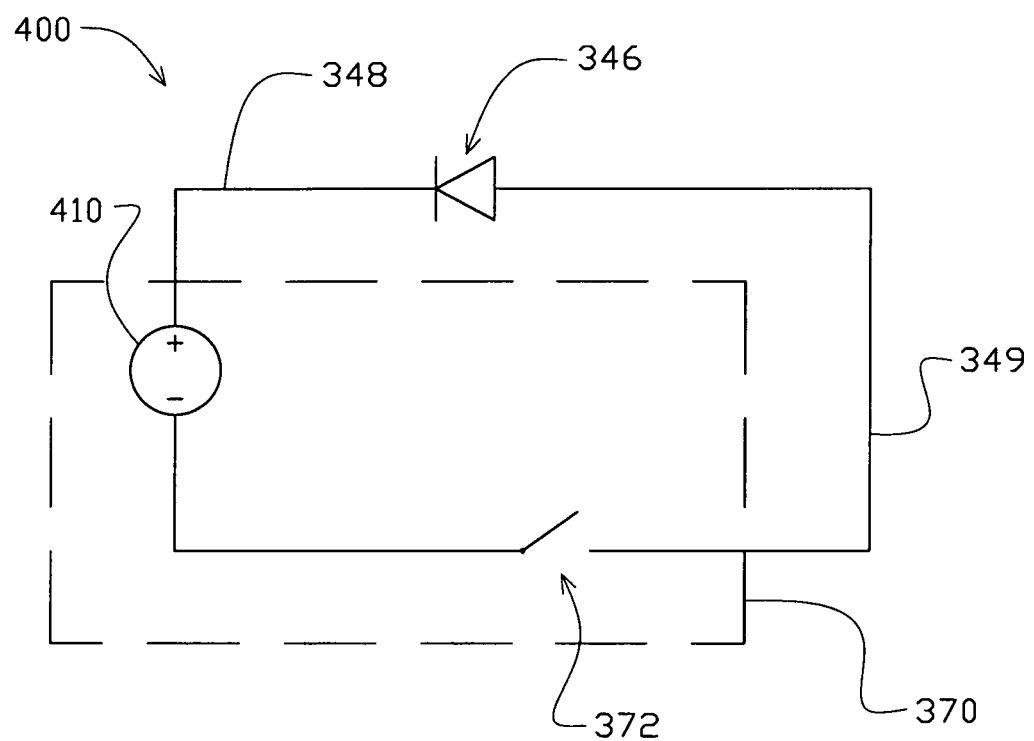
FIG. 4 is a schematic circuit of an alternative embodiment of the invention.

FIG. 4 is a schematic circuit 400 of an embodiment of the invention illustrated in FIGS. 3*a* and 3*b*. The circuit 400 includes a power source 410, which could be a battery or a capacitor, for example, and the power source 410 is preferably secured proximate to a switch embodied as a detentable portion 372, such as being located in the terminus 370 of the piston 350. Accordingly, the detentable portion 372 is illustrated as and effectively performs the function of a switch. In the embodiment illustrated in FIGS. 3*a* and 3*b*, a first wire 348 and a second wire 349 are shown as components that complete the circuit 400, and are each electrically coupled between the switch 372 and the power source 410 in a manner known to those of skill in the electrical arts. The function and alternative structures of the invention are readily apparent to those of skill in the art upon reading the present disclosure.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

I claim:

1. An apparatus, comprising:
   a needleless syringe, comprising
      a generally cylindrical tubing having a generally open first end, a second end, and an inner circumference defining a chamber,
      a first flange located at the first end of the tubing, the first flange adapted to accommodate a human finger,
      the second end of the tubing narrowing into a neck, the neck having a channel that is fluidly coupled to the chamber;
   a plunger, comprising
      a shaft having a first end and a second end,
      the first end of the shaft terminating at a piston having an outer circumference flush with the inner circumference of the syringe,
      the second end of the shaft terminating at a terminus having a pressure-detentable push-button switch thereon, the terminus also having therein a power-source,
      a sleeve accommodating a first wire and a second wire, the sleeve substantially transversing the length of the shaft from the terminus to the piston; and
   a circuit, comprising
   the power source secured in the terminus,
   a light source proximate to the piston,
   the first wire electrically couples the light source to the power source through the sleeve, and
   the second wire extending from the light source through the sleeve and to the pressure-detentable push-button switch, such that the second wire electrically couples the light source to the power source when the pressure-detentable push-button switch is compressed.

2. The apparatus of claim 1 wherein the light source is an LED.

3. The apparatus of claim 1 wherein the light source is a programmable LED.

4. The apparatus of claim 1 wherein the piston is translucent.

5. The apparatus of claim 4 further comprising a soft translucent tip coupled to the piston.

\* \* \* \* \*